United States Patent
Brohm-Schmitz-Rode (10) Patent No.: US 11,364,141 B2
(45) Date of Patent: Jun. 21, 2022

(54) UTEROTUBAR IMPLANT DEVICE

(71) Applicants: Andrea Brohm-Schmitz-Rode, Aachen (DE); Heinz Gerhards, Herzogenrath (DE)

(72) Inventor: Andrea Brohm-Schmitz-Rode, Aachen (DE)

( * ) Notice: Subject to any disclaimer, the term of this patent is extended or adjusted under 35 U.S.C. 154(b) by 606 days.

(21) Appl. No.: 15/775,755

(22) PCT Filed: Nov. 14, 2016

(86) PCT No.: PCT/EP2016/077611
§ 371 (c)(1),
(2) Date: May 11, 2018

(87) PCT Pub. No.: WO2017/081329
PCT Pub. Date: May 18, 2017

(65) Prior Publication Data
US 2018/0369013 A1      Dec. 27, 2018

(30) Foreign Application Priority Data

Nov. 13, 2015   (DE) ...................... 10 2015 119 639.5

(51) Int. Cl.
  *A61F 6/22*    (2006.01)
  *A61B 17/12*   (2006.01)
  *A61F 6/24*    (2006.01)

(52) U.S. Cl.
  CPC ........ *A61F 6/225* (2013.01); *A61B 17/12031* (2013.01); *A61B 17/12163* (2013.01); *A61B 17/12172* (2013.01); *A61F 6/24* (2013.01)

(58) Field of Classification Search
  CPC ...... A61F 6/18; A61F 6/20; A61F 6/22; A61F 6/06; A61F 6/00; A61F 6/08; A61F 6/12;
  (Continued)

(56) References Cited

U.S. PATENT DOCUMENTS

| 6,634,361 B1 | 10/2003 | Nikolchev et al. |
| 7,975,697 B2 | 7/2011 | Callister et al. |

(Continued)

FOREIGN PATENT DOCUMENTS

| CA | 2381912 | 3/2001 |
| DE | 91 09 006.7 | 10/1991 |

(Continued)

OTHER PUBLICATIONS

Atraumatic definition, Merriam Webster Dictionary, https://www.merriam-webster.com/medical/atraumatic (Year: 2021).*

(Continued)

*Primary Examiner* — Tarla R Patel
(74) *Attorney, Agent, or Firm* — HoustonHogle LLP (57) ABSTRACT

According to the invention, an uterotubal implant device is provided. Said uterotubal implant device comprises at least two compressible self-expanding bodies which are composed of a grid structure and are coupled to one another in a longitudinal direction such that one body is arranged distally in the longitudinal direction and the other body is arranged proximally in the longitudinal direction, at least one of the bodies having a spindle- or funnel-shaped design.

17 Claims, 4 Drawing Sheets

(58) Field of Classification Search
CPC .. A61F 6/14; A61F 6/142; A61F 6/144; A61F 6/146; A61F 6/148; A61F 6/225; A61F 6/24; A61F 17/12031; A61F 17/12172; A61M 25/00; A61B 17/12; A61B 17/1204; A61B 17/12163
USPC ........ 128/830, 831, 832, 833, 839, 836, 834
See application file for complete search history.

(56) References Cited

U.S. PATENT DOCUMENTS

| | | | |
|---|---|---|---|
| 7,987,853 B2* | 8/2011 | Swann | A61F 6/225 |
| | | | 128/831 |
| 8,235,047 B2 | 8/2012 | Swann et al. | |
| 8,322,341 B2 | 12/2012 | Koeller | |
| 9,016,280 B2* | 4/2015 | Tal | A61F 6/20 |
| | | | 128/831 |
| 2005/0274384 A1 | 12/2005 | Tran et al. | |
| 2007/0020311 A1* | 1/2007 | Browning | A61K 9/0039 |
| | | | 424/426 |
| 2007/0056591 A1 | 3/2007 | McSwain | |
| 2010/0076463 A1* | 3/2010 | Mavani | A61B 17/1219 |
| | | | 606/151 |
| 2010/0192959 A1 | 8/2010 | Shandas et al. | |
| 2011/0108039 A1* | 5/2011 | Frigstad | A61F 6/22 |
| | | | 128/831 |
| 2011/0144417 A1* | 6/2011 | Jagger | A61F 2/0063 |
| | | | 600/30 |
| 2012/0067352 A1 | 3/2012 | Gruber et al. | |
| 2012/0192872 A1* | 8/2012 | Rudakov | A61F 6/146 |
| | | | 128/831 |
| 2013/0186409 A1 | 7/2013 | Frigstad et al. | |
| 2013/0220336 A1 | 8/2013 | Gopal et al. | |
| 2013/0310683 A1 | 11/2013 | Swann et al. | |
| 2013/0312763 A1 | 11/2013 | Brenzel et al. | |
| 2014/0276915 A1* | 9/2014 | Stout | A61L 31/145 |
| | | | 606/119 |
| 2015/0201945 A1 | 7/2015 | Wijay | |
| 2016/0030109 A1* | 2/2016 | Truckai | A61B 17/12159 |
| | | | 623/23.75 |

FOREIGN PATENT DOCUMENTS

| | | |
|---|---|---|
| DE | 92 05 797.7 | 6/1992 |
| DE | 600 20 719 | 3/2006 |
| EP | 0 533 511 | 3/1993 |

OTHER PUBLICATIONS

Spindle defintiion, Dictionary.com, https://www.dictionary.com/browse/spindle?s=t(Year: 2021).*

International Search Report and Written Opinion, dated Dec. 23, 2016, from International Application No. PCT/EP2016/077611, filed on Nov. 14, 2016. 13 pages.

International Preliminary Report on Patentability, dated May 15, 2018, from International Application No. PCT/EP2016/077611, filed on Nov. 14, 2016. 9 pages.

Schmitz-Rode, T., et al., "Self-expandable spindle for transcatheter vascular occlusion: in vivo experiments," Work in progress. Radiology., 188 (1): 95-100 (1993).

Schmitz-Rode. T., et al., "Experimental nonsurgical female sterilization: transcervical implantation of microspindles in fallopian tubes," J. Vasc. Interv. Radiol., 5 (6): 905-10 (1994).

* cited by examiner

UTEROTUBAR IMPLANT DEVICE

RELATED APPLICATIONS

This application is a § 371 National Phase Application of International Application No. PCT/EP2016/077611, filed on Nov. 14, 2016, now International Publication No. WO 2017/081329, published on May 18, 2017, which International Application claims priority to German Application 10 2015 119 639.5, filed on Nov. 13, 2015, both of which are incorporated herein by reference in their entirety.

The present invention is related to a uterotubal implant device and a minimally invasively placeable implant for the closure of a fallopian tube for contraception.

The possibility of long-term contraception is helpful and desirable for certain individual social and medical constellations. There are various methods for long-term prevention.

Intrauterine devices (IUD) are known for contraception, also known as "contraceptive coil". These are objects that are inserted into the uterus of the woman and prevent pregnancy by mechanical stimulus of the uterine mucosa, change of environment or thickening of the cervical mucus.

There are several types of contraceptive coils that are distinguished, most of which are made of plastics.

On the one hand, this is a classic contraceptive coil with an overlay of a copper silver wire or gold and on the other hand a contraceptive coil with a hormone-releasing plastic cylinder.

Copper-containing contraceptive coils are also intended to kill or deactivate sperm by secreting the smallest amounts of copper. IUDs are considered very safe and long-term contraceptive methods. An example of this is the copper coil. This is a plastic body that has copper, which acts nidation-preventive, and is introduced into the uterus. As an alternative to the conventional copper coil, a "copper chain" (GyneFix) is known. This consists of copper cylinders lined up on a thread and is fixed to the uterine wall so that slipping or expulsion becomes less likely.

In addition to the mechanism of action of the copper component, the copper-silver coil should exert an antibacterial and fungicidal effect triggered by the silver content. Another variation is the copper-gold coil. It has a gold core and acts essentially like the copper-silver coil.

All contraceptive coils must be changed at least every 3 to 5 years, depending on the product.

Even if properly inserted, the uterine wall may in rare cases be injured or punctured due to its individual nature. Immediately after insertion, minor bleeding and pain as well as a slowed pulse may occur in the short term. Expulsion of the contraceptive coil, especially during heavy menstruation, is possible in some patients. The coil can change its position as a result of movements of the uterine musculature and, rarely, penetrate into the uterine wall or walk through it. Then it has to be surgically removed.

A hormone coil (Mirena®) is a hormonal (corpus luteum hormone-containing) long-term contraceptive that is introduced into the uterus. The immediate proximity to the site of action results in a very small amount of hormones, with the active substance triggering a similar mechanism of action as the corpus luteum hormone pill: the cervical mucus becomes impermeable to sperm. If, however, a sperm reaches the fallopian tube, fertilization is usually prevented there. And finally, if still an egg has been fertilized, it will prevent nidation into the uterine cavity. The product must be replaced every 5 years at the latest.

Another possible method is the occlusion of both fallopian tubes by one implant each. The implant can be, hysteroscopically or fluoroscopically guided, introduced into the uterotubal junction and the proximal fallopian tube via a thin catheter after in a compressed state and unfolded there. After deployment, the implant should remain in the proximal fallopian tube and uterotubal junction and grow into the uterotubal mucosa. The closure effect is thus initially mechanical. By a drug doping of the implant or its subcomponents an additional pharmacological effect can be achieved as long as the drug is effective.

In the context of interventional radiology, small, transcatheterally applicable balloons or metal spirals are used for the embolization of vessels. Often, however, the cross-sectional blockage achieved with a coil is not sufficient to produce a secure closure. The disadvantage of the detachable balloon consists in a partially insufficient fixation on the vessel wall, whereby it can take an unwanted localization after placement.

In the context of transuterine tubal sterilization with the hysteroscope, tube closures have already been described by electrocoagulation, by application of tissue adhesive and by means of spouts made of silastic gum. All three methods have in common that they do not provide safe contraception and that they are usually not reversible.

From DE 91 09 006 U1 "atherectomy angioplasty catheter" a catheter is known which has at the top a self-expandable basket of a braided tubular mesh. The mesh basket is firmly connected to the catheter in this device. The system serves to reopen vascular occlusions and is introduced into the vascular system only for the duration of the treatment.

In DE 92 05 797 U1 a self-expandable mesh basket for the closure of human hollow organs is described. This mesh basket is a spindle-shaped occlusion body which can be used as a transuterinely delivered intratubal contraceptive. It should also be able to produce a vascular occlusion in the context of an interventional embolization therapy.

Such a uterotubal implant, which comprises a body closed on both sides, which is formed from a tubular wire mesh, is also described in Schmitz-Rode T, Timmermans H, Uchida B, Kichikawa K, Nishida N, Günther R W, Rosch J. Self-expandable spindle for transcatheter vascular occlusion: in vivo experiments. Work in progress. Radiology. 1993 July; 188 (1): 95-100; and Schmitz-Rode T, Ross P L, Timmermans H, Thurmond A S, Günther R W, Rosch J. Experimental nonsurgical female sterilization: transcervical implantation of microspindles in fallopian tubes. J Vasc Interv Radiol. 1994 November-December; 5 (6): 905-10.

A similar uterotubal implant is disclosed in US 2005/0274384 A1. According to an alternative embodiment, it is also possible to provide two lattice-shaped, cylindrical self-expanding bodies which can be arranged one behind the other in a longitudinal direction and which are designed to taper conically at their distal ends.

US 2013/0220336 A1 discloses a uterotubal implant. This uterotubal implant comprises a metal coil connected at a distal end to a wire centrally disposed in the coil.

US 2013/0186409 A1 discloses an implant comprising a self-expanding stent. This device has struts, by means of which the fallopian tube should be closed by "stretching".

U.S. Pat. No. 6,634,361 B1 describes an occlusion body which comprises a central wire on which two expandable spiral-shaped bodies are arranged.

U.S. Pat. No. 7,975,697 B2 discloses various fallopian tube implants.

U.S. Pat. No. 7,987,853 B2 and US 2013/0310683 A1 disclose uterotubal implants which are formed from a plurality of individual stents which are coupled to one another via connecting means. After insertion of the stents, the connecting means are removed.

U.S. Pat. No. 8,235,047 B2 discloses a closure device which has a plurality of expandable bodies which can be introduced into the body via a connecting means detachably connected thereto.

In U.S. Pat. No. 8,322,341 B2, an implant for occluding a body lumen is disclosed, comprising a distally arrangeable first body, wherein after the arrangement of the first body, a second, funnel-shaped body is insertable and arrangeable in the longitudinal direction proximal to the first body. However, these two bodies are not coupled to each other, but slidably arranged to each other.

In US 2015/0201945 A1 a device for closing a lumen, such as a fallopian tube is disclosed. The device is not self-expanding and therefore has an actuator for expansion. Furthermore, this device comprises a closure body which is formed by longitudinal struts, which are surrounded by an impermeable wrap. In the distal region, the body has an approximately spindle-shaped section. In the proximal region of the closure body, the longitudinal struts form a substantially cylindrical anchor or fixation section. The anchor portion is intended to provide additional stability to the device by increasing the area by which the device is fixable in a lumen. Attached to the distal end of the device is an actuation strand of the actuator extending through the section. By operating the strand, the tubular section is expandable. By forming the body from substantially longitudinal struts, the device has a high axial rigidity. A resulting non-physiological axial extension of the curved fallopian tube may cause discomfort in the patients.

DE 600 20 719 T2 discloses an actuating system for the deployment of a contraceptive agent in the fallopian tube.

The object of the present invention is to provide a uterotubal implant device which enables a reliable closure of the fallopian tube for contraception and which can be easily introduced into the human body and adapted to the implantation site, which is fixable thereto and also removable from the body.

This object is achieved by the independent claim. Advantageous embodiments are specified in the subclaims.

According to the invention, a uterotubal implant device is provided. This uterotubal implant device comprises at least two compressible self-expandable bodies, the bodies being formed of a grid structure and coupled together in a longitudinal direction such that one body is longitudinally distal and the other body longitudinally proximal, in which at least one of the bodies is spindle-shaped or funnel-shaped.

The fact that the device comprises at least one distal and one proximal body, wherein at least one of the bodies has a spindle-shaped or funnel-shaped design, allows the device to be optimally adapted to the bending and the diameter of a fallopian tube. This means that the device is optimally adaptable in a simple way to a hollow organ wall, in particular to a fallopian tube wall, and provides an optimum fit. Due to the optimal fit, a good anchorage with the tissue of the fallopian tube adjacent to the device is also possible.

In the context of the present invention, a coupling of the bodies is understood to mean that the bodies of the device according to the invention are connected to one another both before insertion and after insertion. The connection can preferably take place along a central longitudinal axis of the body.

In the context of the present invention, a grid structure of the bodies may be understood to mean an approximately uniform structure which comprises intersecting struts which overlap or are connected to one another in the region of crossing points.

The bodies may have a predetermined radial expansion force in the expanded state. This radial expansion force is large enough to slightly expand the fallopian tube section. A region of the body, which then rests in the expanded state on the corresponding fallopian tube section, is referred to as the contact portion and is formed on an outer wall of the body towards the fallopian tube wall. The contact portion contacts the Fallopian tube wall such that it generates a mechanical stimulus such that at least a part of the contact portion of the body undergoes ingrowth into the Fallopian tube wall. At the same time, the corresponding grid structure contacts the fallopian tube section in a uniform and atraumatic manner such that the fallopian tube wall is not irritated except for the ingrowth stimulus and, in particular, injury or perforation of the fallopian tube wall is avoided.

The at least two to four and preferably three bodies may also have different radial expansion forces to adapt to the curvature of the fallopian tube.

The distal and proximal bodies may preferably have a larger diameter and a greater radial expansion force than the middle body or bodies. The middle body or bodies are located in the most pronounced constriction of the fallopian tube (intramural portion), the distal and proximal bodies are located in the fallopian tube behind or in front of it. In this way dislocation of the implant is prevented. A dislocation (in both directions) would only be possible if one of the outer bodies with large radial expansion force would be able to traverse the intramural section. This is prevented by the larger diameter and larger radial expansion forces of the distal and proximal bodies relative to the middle body or bodies.

The bodies may preferably be rotationally symmetrical.

Due to the arrangement and the design of its tubular, preferably rotationally symmetrical walls, the implant according to the invention has a good adaptability to the individual uterotubal anatomy. On the one hand, the at least two bodies enable firm anchoring in the fallopian tube and, on the other hand, they are so compliant and flexible that no chronic pain and inflammatory reactions occur.

The adaptability to the fallopian tube, which is a hollow organ with inter-individually (patient to patient) different curvatures and changing diameters, results from the axial coupling and arrangement of the individual bodies, as well as by the outer walls of the grid structures of the bodies, which, due to their radial expansion force, form the largest possible contact surface with the fallopian tube inner wall, with uniform expansion pressure (punctually high pressure on the fallopian tube wall would promote perforation). A self-expandable tubular grid structure is advantageous because it can be gradually adjusted with respect to the spring effect of its radial expansion, so that it can be optimally matched to the compliance (in the physiological sense: $\Delta V/\Delta p$) of the hollow organ (fallopian tube). An optimum is achieved if the implant is not too tight, otherwise there would be the risk of trauma, necrosis, and perforation, but also not too loose, otherwise the implant would slip out of the fallopian tube or would not close it properly.

Under hysteroscopical or fluoroscopical guidance the implant can be introduced into the uterotubal junction and the proximal fallopian tube via a thin catheter in a compressed state and unfolded there. After deployment, the implant remains stationary in the proximal fallopian tube and the uterotubal junction and grows into the uterotubal mucosa. The closure effect is thus initially mechanical. With an additional pharmacological doping of the implant or of its subcomponents, an additional pharmacological effect can be achieved as long as the drug is effective.

In the device according to the invention, in contrast to the device disclosed in US 2015/0201945 A1, it is advantageous that the bodies of the device, due to their self-expandable grid structure, their shape and their low axial stiffness and their adjusted radial expansion force and compliance, adapt to the wall of the lumen of the fallopian tube with the greatest possible contact surface area and therefore usually cause no discomfort in the patient after implantation. Thus, when using the device according to the invention, there is no non-physiological axial straightening of the curved fallopian tube and no punctual high load onto the fallopian tube wall, which could lead to trauma, perforation or necrosis. Thus, the device according to the invention offers a high degree of "wearing comfort" and a complaint-free use.

The bodies may have different diameters in the expanded state, wherein the distal body in the expanded state may have a smaller diameter than the proximal body. In the expanded state, the proximal and distal bodies may preferably have a larger diameter than the middle body or the middle bodies. The diameter of a body is considered in the region where the outer wall of the body has the largest diameter in the expanded state.

The intramural part of the fallopian tube running in the uterine wall has the smallest diameter. While it has a funnel-shaped opening towards the uterine cavity (uterotubal junction), the diameter inside the uterine wall can be less than 1 mm. This is followed by the so-called isthmic part of the fallopian tube. It is 2 to 3 cm long, has a diameter of 2 to 3 mm with a tendency to a larger diameter more distal, where the ampullary section with a diameter of 4 to 10 mm follows. The isthmic part has a pronounced wall musculature which, due to its contraction, can act on an implant located there with the risk of removing it by peristaltic activity.

The said fallopian tube sections are closed with the device according to the invention. The fallopian tube section provided for the implant is thus a hollow organ with a very narrow segment. Proximal of it is the uterine cavity, distally the relatively wide ampullar part of the fallopian tube. Therefore, the shape formation of the device allows optimal adaptability to the shape or geometry of the fallopian tube in this section.

In the preferred embodiment, the device includes longitudinally from distal to proximal a first larger diameter body intended for implantation in the isthmic portion, a second smaller diameter body for implantation in the intramural portion, and a larger diameter proximal body for implantation in the uterine cavity. The proximal body may in turn have a larger diameter than the distal body.

If the implant according to the invention is formed only of two bodies, they are arranged such that the most pronounced constriction of the fallopian tube is arranged between these two bodies. In this way, the implant is not dislocated by the motility of the tubal musculature (i.e., neither expelled into the uterine cavity nor displaced into the ampullary portion). That means, the proximal body is sized that large in diameter that complete retraction of the implant into the fallopian tube is prevented, and the distal body is sized that large in diameter such that complete expulsion of the implant into the uterine cavity is prevented. Accordingly, as described above, when the device is formed of three bodies, the distal and proximal bodies may have a larger diameter than the central body or bodies to prevent dislocation.

One of the bodies may be spindle-shaped and the other body may be funnel-shaped.

According to this preferred embodiment, the device according to the invention comprises three bodies, wherein all three bodies are spindle-shaped. Alternatively, the middle and the distal body may be spindle-shaped and the proximal body may be funnel-shaped. Alternatively, the proximal and the central body may be spindle-shaped and the distal body may be funnel-shaped. Also, the spindle shape is favorable to prevent dislocation, since it provides an approximately cylindrical outer wall surface, which adapts relatively evenly with a well-dosed spring force (compliance) to the fallopian tube wall. Alternatively, the proximal and the distal body may be funnel-shaped and the central body may be spindle-shaped. The proximal body may then be conically widening from distal to proximal or from proximal to distal. The distal body may then be conically widening from distal to proximal or from proximal to distal. However, it is preferred that, according to such a design of the device, the proximal body is designed to expand from distal to proximal and the distal body to widen conically from proximal to distal. This extremely effectively prevents dislocation of the device in the fallopian tube. In contrast, the funnel shape blocks a dislocation because the implant thus wedges in the fallopian tube wall. The natural movement of the fallopian tube to "milking out" of an egg (but also of the implant) can go in both directions, but especially in the direction of the uterine cavity. Thus, the formation of the device with two such "blocking funnels" at both ends can be ideal.

Another effective way to prevent dislocation, as indicated above, is to provide the larger diameters and the greater radial expansion forces on the outer spindle-shaped bodies, which are arranged such that the narrow intramural portion is located precisely between these two outer bodies.

In the context of the present invention, a spindle-shaped body is understood to mean a body which has the largest diameter in its center with respect to the longitudinal direction and which is conically flared at its proximal end and conically tapered at its distal end such that the body forms a spindle shape, or is formed approximately elliptical in its longitudinal section. That is, the body has the smallest diameter at its distal and proximal ends. That is, the distal and proximal ends of the spindle-shaped body are approximately strand-like, formed by consolidation (i.e., permanent axial compression, for example, by pulling on a sleeve, by brazing, welding, or gluing) the grid structure. Such a consolidation section limits the bodies and forms the transition from one body to the next body.

The region of such a body, which is arranged between the proximal end and at the distal end can also be formed approximately cylindrical.

A funnel-shaped body is a body that is longitudinally expanded from distal to proximal or from proximal to distal over its entire or over its substantially entire length conically widening. A reverse arrangement is also possible. A funnel shape is also understood to mean bell-shaped or conical shapes with different angles of inclination with respect to the longitudinal direction.

Furthermore, a flexible connecting wire and/or connecting wire sections can be provided, via which the bodies are coupled to one another.

The connection wire or the connecting wire sections serve as spacers similar to the strand region or regions in which the bodies are coupled to one another, which defines the spacing of the individual bodies in the longitudinal direction relative to one another. In addition, the bodies are coupled to one another via the connecting wire or the connecting wire sections. The connecting wire or the wire sections absorb pressure and tensile forces in order to maintain the arrangement of the bodies relative to one another and to prevent dislocation of the implant, whereby the wire itself should be designed to be flexible in order to adapt to curvatures of the fallopian tube.

The connecting wire or wire sections may extend longitudinally through the bodies, in which case the bodies are connected to the connecting wire at least at their proximal and/or distal ends such that the coupling of the bodies is by means of the connecting wire.

Furthermore, the bodies can be coupled to one another by means of connecting wire sections in the manner of a pearl necklace. That is, a distal or a proximal end of a body is coupled to a proximal or a distal end of another body via a connecting wire section. The connecting wire or the connecting wire sections are flexible in the radial direction and exert a certain rigidity in the longitudinal direction with respect to pressure and tension load.

For example, a proximal end of a spindle-shaped body may be coupled to the connecting wire by a tubular sleeve such that the proximal end of this body is longitudinally slidably connected to the connecting wire. A distal end of a spindle-shaped body may, for example, be fixedly connected to the connecting wire by means of a tubular sleeve. A reverse arrangement is also possible.

Thus, a distal and/or a proximal end of a spindle-shaped body or a merged end of a funnel-shaped body may be coupled to a connecting wire section to connect this body to another body of the implant.

By the displaceability of a preferably proximal end or the distal end of the spindle-shaped body with respect to the connecting wire in the longitudinal direction, it is possible that the corresponding body can transform from a compressed to a radially expanded state and vice versa. This is particularly important when inserting the device according to the invention in the fallopian tube by means of a catheter, since the bodies in the compressed state have a substantially greater extent in the longitudinal direction, meaning a greater length, than in the expanded state, in which the length is reduced due to the expansion in the radial direction.

The device according to the invention comprises at least two or three or four or five or six or more, in particular two to four and preferably three self-expandable bodies.

All bodies can be spindle-shaped. It is also possible that all bodies are funnel-shaped. Combinations of spindle-shaped and funnel-shaped bodies are also advantageous. The preferred embodiments of the bodies will be described in more detail below in the embodiments.

The length of the device from the distal end of the distal body to the proximal end of the proximal body is about 10 mm to 70 mm or 20 mm to 60 mm or 35 mm to 45 mm, respectively.

Thus, the length of the implant is preferably less than 50% based on a total length of a fallopian tube of from about 10 cm to 16 cm.

The bodies have in the expanded state in the areas of their greatest extent transverse to the longitudinal direction of the device a diameter of about 1 to 3 mm.

The bodies may have different diameters in the expanded state, wherein a body which is arranged in the uterine cavity or in the uterotubal junction, is referred to as a proximal body, which has a diameter of about 3 mm to 4 mm, and preferably of 3 mm and/or one or two bodies are provided for implantation in the intramural portion and the body or bodies referred to as the middle body or middle bodies having a diameter of about 2 mm and a body for implantation in the isthmic section, this body being called a distal body, and the distal body having a diameter of about 3 to 4 mm, and preferably of 4 mm.

The bodies may be braided from one or more wires or made from a tubular body by laser cutting.

As braided wire, a nitinol wire (shape-memory alloy) is preferably provided. The shaping during tempering of the shape-memory alloy can influence or set the radial expansion force.

The individual bodies can be formed in which a continuous braid, which is a basic structure of the device, is punctually compressed, for example by pulling on a sleeve, by laser welding or soldering or gluing.

The device or its bodies may alternatively be made of a tube, for example of nitinol (shape memory alloy nickel-titanium), by means of laser cutting. Subsequently, the shape to be produced is restamped in the expanded state on the tube. The connection points between the bodies arise either secondarily by selective compression of the expanded tube (fixed by pulling a sleeve, by laser welding, by soldering or gluing) or primarily by leaving as a short tube section with a small initial diameter not processed by laser cut.

In laser cutting, the radial expansion force can be adjusted by the following parameters:
  through the cutting pattern of the laser cut grid, and
  by the diameter, the thickness and the material of the tube semi-finished product and its shaping during tempering, preferably using a shape memory alloy such as nitinol.

Such a laser-cut device is also arranged in the implantation catheter in the compressed state and expands independently, which means, is self-expanding after the catheter has been removed or after which the device has been released.

The openings of the grid structure or of the cut bodies preferably have an opening width or a strut spacing of less than 1 mm or from 200 µm to 700 µm, in particular from 300 µm to 600 µm. In a production by braiding of individual wires the grid structure or strut formed *rhombi* tend to be longer in the axial direction, if a braid angle less than 45°, or shorter, if a braid angle greater than 45° was used.

The outer surfaces of one or more bodies may be completely or at least partially coated. The type and structure of the coating will be described in more detail below.

The coating may, for example, be a swellable hydrogel which is doped with a bioactive agent. The active ingredient may, for example, a spermicide, such as Nonoxinol-9. Furthermore, such an active ingredient may be an anti-progesterone, which reduces the tendency to bleed and promotes or supports the ingrowth of the implant into the fallopian tube wall.

Furthermore, the spindle-shaped bodies may be filled with a closure promoting material, which may also be doped with a bioactive agent. The type and construction of the closure promoting material will be described in more detail below.

In the case where swelling fibers or the like are provided as the closure-promoting material, its swelling property leads to an increase in the closing effect of the device on contact with liquid.

In providing a hydrogel or the like as a closure promoting material, doped with, for example, a bioactive agent, this doping can contribute to the reduction of sperm motility, so that the contraceptive effect is enhanced.

Furthermore, fibers can be woven into the grid structure. The fibers can be provided to increase the spermicidal effect and be formed of copper or to increase the closing effect of swellable polymer fibers.

Weaving in the context of the present invention also means braiding or otherwise introducing the fibers between the grid structure.

At the distal end of the distal implant, a probe tip can be provided, which is designed, for example, as an atraumatic ball. Such an atraumatic ball facilitates insertion of the device to the site of implantation and prevents injury to the tissue surrounding the device when inserted. Such an atraumatic ball may be connected to the distal end of the implant via a straight or curved wire section.

In principle, the other bodies of the implant, except for a spindle-shaped or funnel-shaped body, can also have other shapes which are suitable for adaptation to the shape of the fallopian tube, for example, approximately spherical or cylindrical.

The invention will be explained in more detail below with reference to the drawings. These show in FIG. 1 shows a uterotubal implant device according to the invention in a state introduced at the implantation site, in a fallopian tube respectively.

A uterotubal implant device 1 according to the invention comprises at least two compressible self-expandable bodies 2, wherein the bodies are formed from a grid structure 3. The bodies 2 are coupled together in a longitudinal direction 4 such that one of the bodies 2 is arranged distally 5 in the longitudinal direction and the other body 2 is arranged proximally 6 in the longitudinal direction 4.

Figure 1:
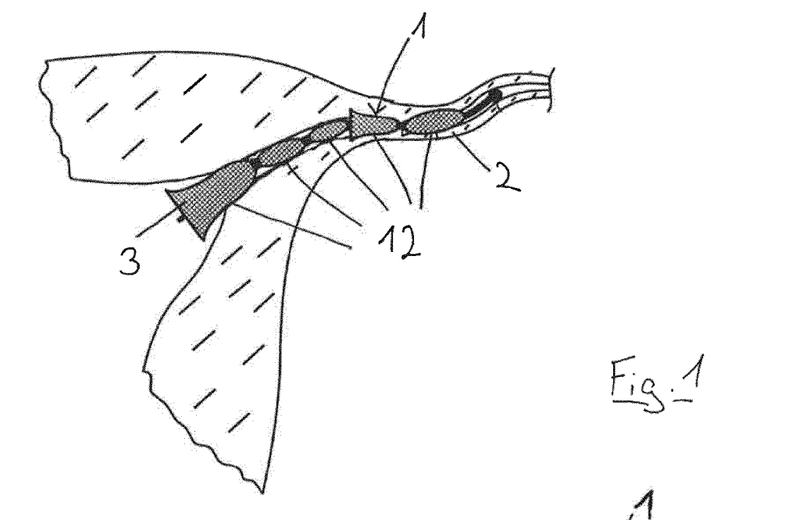
Figure 2:
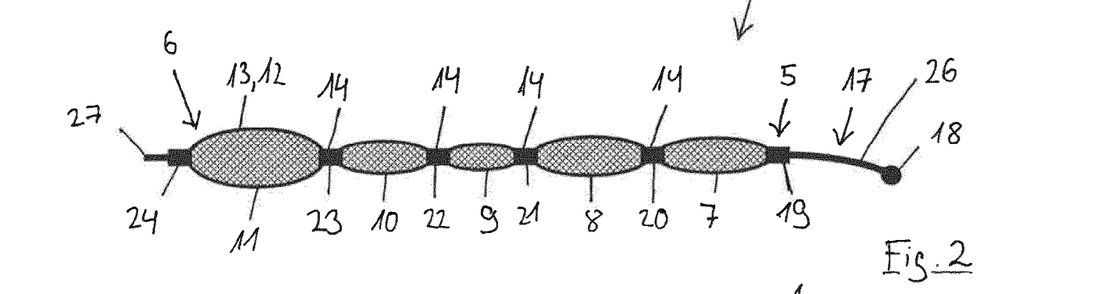
FIG. 2 shows a device according to the invention in a schematic side view.

In the following, the uterotubal implant device 1 according to the invention will be described in more detail with reference to a first exemplary embodiment (FIGS. 1 and 2).

According to this first embodiment, the device 1 comprises in the longitudinal direction 4 from distal 5 to proximal 6 a first and a second body 7, 8, which are intended for implantation in the isthmic section, a third and a fourth body 9, 10 for implantation in the intramural section, and a proximal body 11 for implantation in the uterine cavity.

The bodies 2, 7, 8, 9, 10 and 11 are designed to be compressible and self-expandable. In this way, it is possible to implant the device 1 minimally invasively by means of a thin catheter (not shown). The catheter can be advanced hysteroscopically or under fluoroscopic control to the site of implantation.

The bodies 2, 7, 8, 9, 10 and 11 have a predetermined radial expansion force in the expanded state. This expansion force is large enough or dimensioned so that the bodies can slightly expand a fallopian tube section, which they contact, in order to effect full circumferential contact of the body with the fallopian tube wall. This contact acts as a mechanical stimulus for ingrowth of the bodies into the fallopian tube wall. In addition, the radial expansion force must be dimensioned such that a contact portion 12 (FIGS. 1, 2) of an outer wall of the body 13 contacts the Fallopian tube so that no chronic irritation, perceived as painful, or even penetration of the Fallopian tube occurs. That means, the expansion force must be such that the contact portion 12 of the outer wall 13 of the body atraumatically contacts with the corresponding portion of the Fallopian tube wall.

The bodies 2, 7, 8, 9, 10 and 11 are braided from a plurality of wires so as to form a braided tubular endless structure. This structure is cut to length corresponding to a total length of the device 1 of approximately 35 mm at the proximal and distal ends 5, 6.

At the proximal and distal ends 6, 5 and at four intermediate coupling sections 14, the bodies are constricted or compressed. The compression can be done for example by means of welding spots, gluing or a mounted sleeve.

According to the first embodiment, sleeves 19, 20, 21, 22, 23, 24 are provided. The areas in which the sleeves 20, 21, 22, 23 are arranged form coupling sections 14.

As a braided wire, a nitinol wire (shape-memory alloy) is preferably provided. The shaping during tempering of the shape-memory alloy can influence or set the radial expansion force. Furthermore, the radial expansion force can be influenced by the type of grid structure 3 or the wire mesh of the bodies, the number of wires, the diameter of the wires and the bodies and the braid angle of the wires. It is a braid angle of preferably greater than 35° provided with respect to an axial center axis, in order to achieve a sufficient self-expandability.

The grid openings formed in the grid structure 3 of the bodies preferably have a maximum width or a strut spacing of less than 1 mm, or from 200 µm to 700 µm, in particular from 300 µm to 600 µm.

At the distal end 5 of the implant 1, a probe tip 17 is arranged. The probe tip 17 preferably includes a wire portion 26 and an atraumatic ball 18 disposed thereon.

The struts or braided wires that form the outer surfaces of the bodies are preferably completely or at least partially coated. The coating (not shown) may comprise a polymer, such as e.g. a polyurethane or a biodegradable polylactide or a swellable hydrogel. The coating can in principle be formed from all plastics in which drugs can be stored and which release an active substance over a longer period of time.

Furthermore, the coating can, in particular if a swellable hydrogel is provided, be doped with a bioactive agent. The active ingredient may be, for example, a spermicide, such as Nonoxinol-9. Furthermore, such an active ingredient can be an anti-progesterone, which reduces the tendency to bleed and promotes or supports the ingrowth of the implant into the fallopian tube wall.

The spindle-shaped bodies 2, 7, 8, 9, 10 and 11 according to the first exemplary embodiment are additionally or alternatively to their coating filled with a closure-promoting material (not shown). For example, biocompatible textile fibers of polyethylene terephthalate, polyamide or biodegradable polylactide are provided as closure-promoting material. By a swellability of such fibers in contact with liquid, the closure effect is promoted. The fibers may also be hydrogel impregnated to increase swellability.

Additionally and/or alternatively, the grid structures of the bodies are directly coated with swellable hydrogel. Both the fibers and/or the hydrogel may be doped with a bioactive agent.

Biodegradation of polylactide produces acid degradation products. In such an acidic environment sperm motility is considerably reduced. In this way, the contraceptive effect can be increased.

Additionally and/or alternatively, in order to increase the spermicidal effects, threads may be introduced into the grid structure of the implant bodies by means of weaving or braiding. Here, in particular, copper or polylactide fibers are provided.

Additionally and/or alternatively, swelling polymer fibers can be woven or interwoven into the grid structure to increase the closure effect. It is also possible that the filling described above contains copper in order to increase the spermicidal effect, or contains gold or silver to exert a bactericidal effect.

The length of the device according to the invention from a distal end of the first body 7 to a proximal end of the fifth body 11 is 10 mm to 70 mm or 20 mm to 60 mm and preferably 35 mm to 45 mm.

The bodies are preferably rotationally symmetrical.

Furthermore, the bodies may have different lengths.

According to the first exemplary embodiment, the fifth body 11 which can be arranged in the uterine cavity has a diameter of approximately 3 to 4 mm, and the third and fourth bodies 9, 10 have a diameter of approximately 2 mm in the expanded state, which are provided for implantation in the intramural portion, and the first and the second body 7, 8, which are provided for implantation in the isthmic section, have a diameter of about 3 mm in the expanded state. The tolerance of the expanded bodies is approximately +/−1 mm.

According to an alternative embodiment of the first embodiment (not shown), a connecting wire 16 may also be provided which extends through the bodies in the longitudinal direction 4.

According to this first embodiment, the connecting wire 16 is a single, continuous wire made of metal or plastic. Alternative embodiments of the connecting wire will be described in more detail below. In the case that the connecting wire 16 is formed of plastic, this may for example be made of a biodegradable polylactide.

The bodies 2, 7, 8, 9, 10 and 11 are connected to the connecting wire only at the distal end via a distal sleeve 19. The distal sleeve 19 is fixedly connected to the connecting wire 16.

The remaining sleeves 20, 21, 22, 23 and 24 arranged between the bodies are coupled to the connecting wire such that all distal and proximal ends of the body or the corresponding sleeves 20 to 24 except for the fixedly connected to the connecting wire distal sleeve 19 are slidably connected to the connecting wire in the longitudinal direction.

The connecting wire 16 can also contain copper and/or gold and/or silver or be coated with copper and/or gold and/or silver.

In the following, a second embodiment (FIG. 3) of the present invention will be explained.

Figure 3:
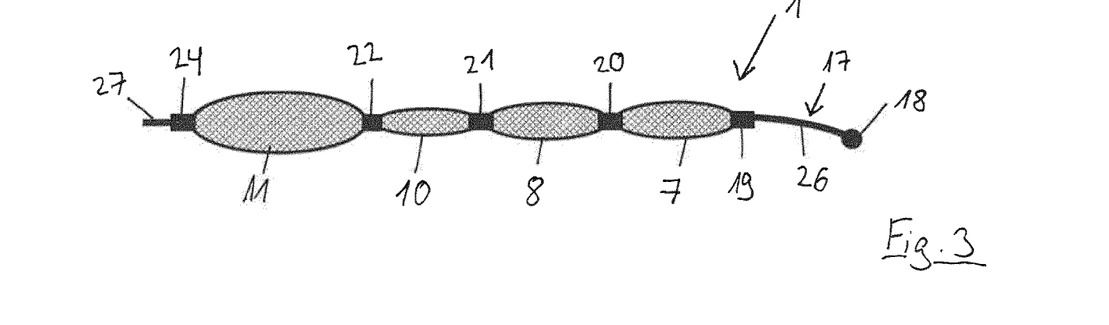
FIG. 3 shows a further exemplary embodiment of the device according to the invention in a schematic side view.

Unless otherwise described, this embodiment corresponds to the first embodiment and includes all features of the first embodiment. Identical parts are provided with the same reference numerals.

According to the second embodiment, only four spindle-shaped bodies are provided instead of five spindle-shaped bodies. In this case, the fourth body was dispensed with, so that the fifth body is arranged immediately after the third body. Here, the fifth body has a greater length in the longitudinal direction than in the first embodiment.

In the following, a third embodiment (FIG. 4) of the device according to the invention will be described. Unless otherwise described, the third embodiment includes the same features as the first embodiment. Identical parts are provided with the same reference numerals.

Figure 4:
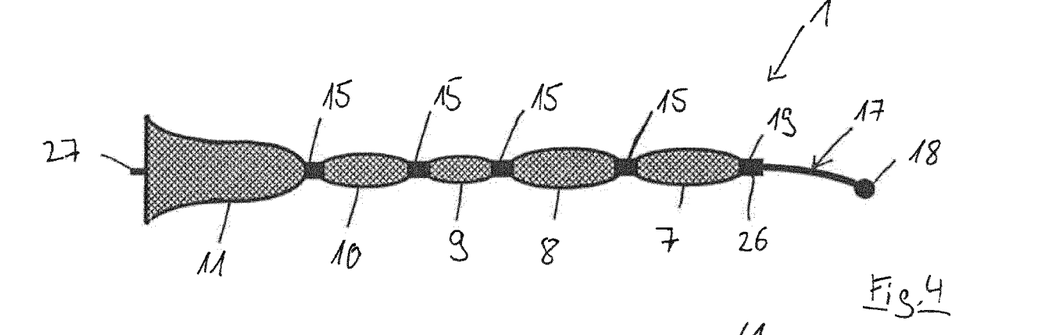
FIG. 4 shows a further exemplary embodiment of the device according to the invention in a schematic side view.

According to the third embodiment, the proximal and the fifth body 11 is not spindle-shaped, but funnel-shaped or, in particular, bell-shaped.

It is provided that a distal end 5 of the fifth body 11 is coupled by means of a sleeve with a proximal end of the fourth body 10.

Figure 5:
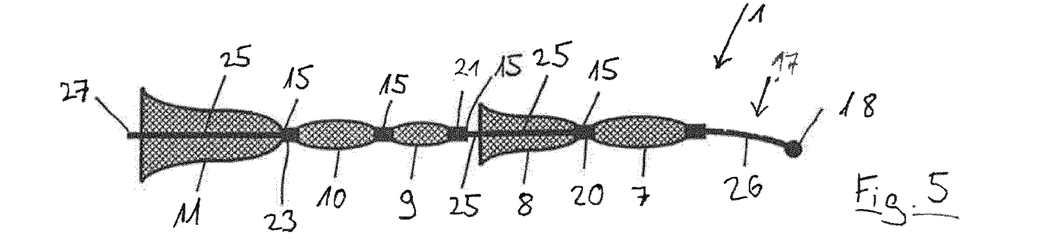
FIG. 5 shows a further exemplary embodiment of the device according to the invention in a schematic side view.

A fourth embodiment of the present invention will now be described (FIG. 5). Unless otherwise described, this embodiment corresponds to the third embodiment and has the same features. Identical parts are provided with the same reference numerals.

In the fourth embodiment, the second body 8 is not spindle-shaped, but bell-shaped. It is provided that the distal sleeve 20 which is arranged at the distal end of the first bell-shaped body 8, is fixedly connected to a connecting wire section 25. The connecting wire portion 25 is fixedly connected to the distal sleeve 21 of the spindle-shaped body 9.

The second bell-shaped body 8 is thus not directly connected to the third body 9 according to this embodiment. The coupling of the two distal bodies 7 and 8 with the three proximal bodies 9, 10, 11 takes place via the connection wire section 25.

The third and the fourth body 9, 10 are again formed spindle-shaped and the fifth body 11 is bell-shaped as described in the third embodiment. It is provided that the fourth body 10 is connected via a proximal sleeve 23 with a distal end of the bell-shaped body 11.

Figure 6:
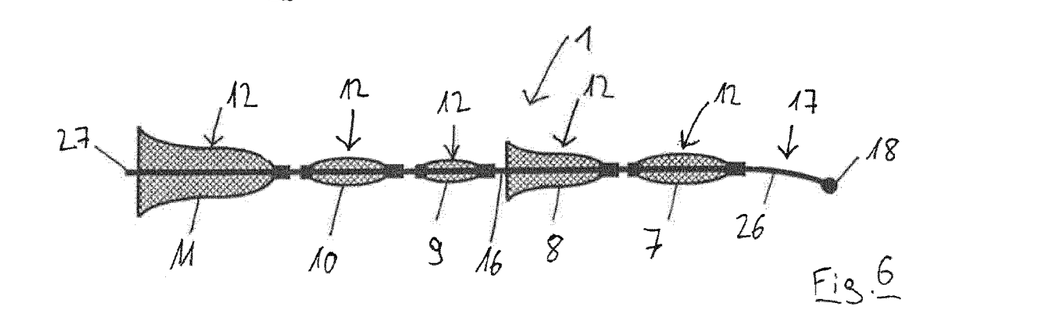
FIG. 6 shows a further exemplary embodiment of the device according to the invention in a schematic side view.

The device according to the invention will be described below with reference to a fifth exemplary embodiment (FIG. 6). Unless otherwise described, this device corresponds to the device described above, in particular it is similar to the fourth embodiment. Identical parts are provided with the same reference numerals.

According to the fifth embodiment, it is provided that all five bodies are individually or separately connected to a continuous connecting wire 16. This means, the first distal body 7 is spindle-shaped and is connected to a distal stationary sleeve and a proximal slidable sleeve to the connecting wire.

The distal end of the bell-shaped second body 8 is fixedly connected to the connecting wire 16 at its proximal end with a proximal sleeve. The third body is fixedly connected at its proximal end to the connecting wire 16 and the proximal sleeve of the third body 9 is slidably connected to the connecting wire. The same applies to the fourth body 10.

The fifth, bell-shaped body 11 is connected according to the second body 8 with the connecting wire.

A first preferred embodiment of the uterotubal implant device 1 according to the invention comprises three compressible self-expandable bodies 2, which are formed from a braided grid structure 3. Unless otherwise described, the preferred embodiment may include all the features of the embodiments discussed above (FIGS. 8 and 9).

Figure 8:
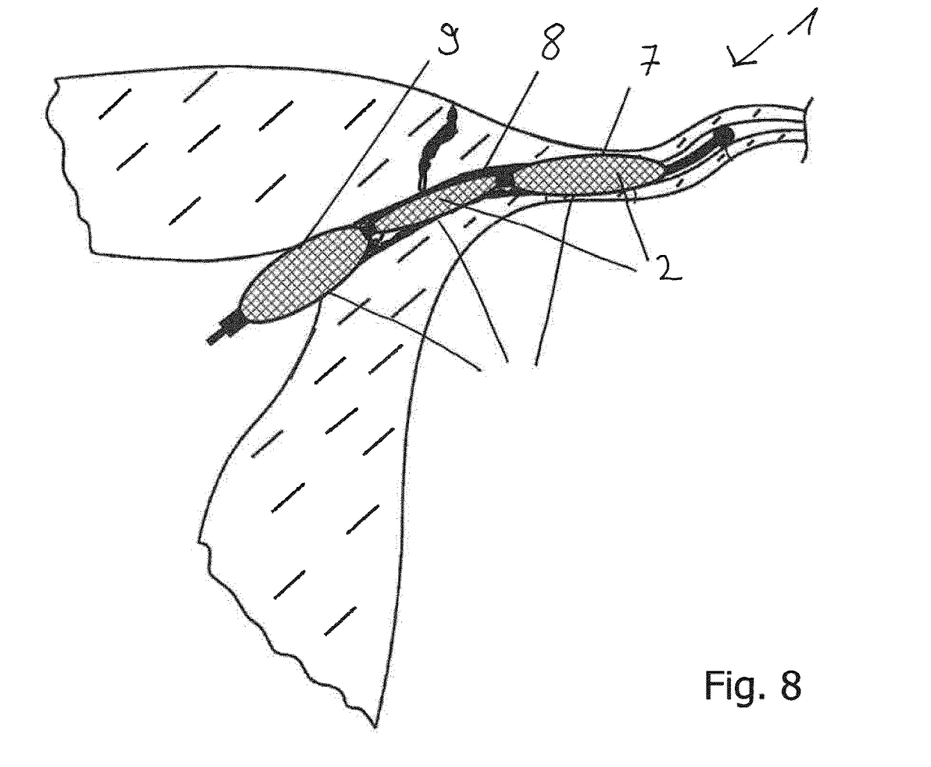
FIG. 8 shows a preferred embodiment of a uterotubal implant device according to the invention in a state introduced at the implantation site, in a fallopian tube respectively.
Figure 9:
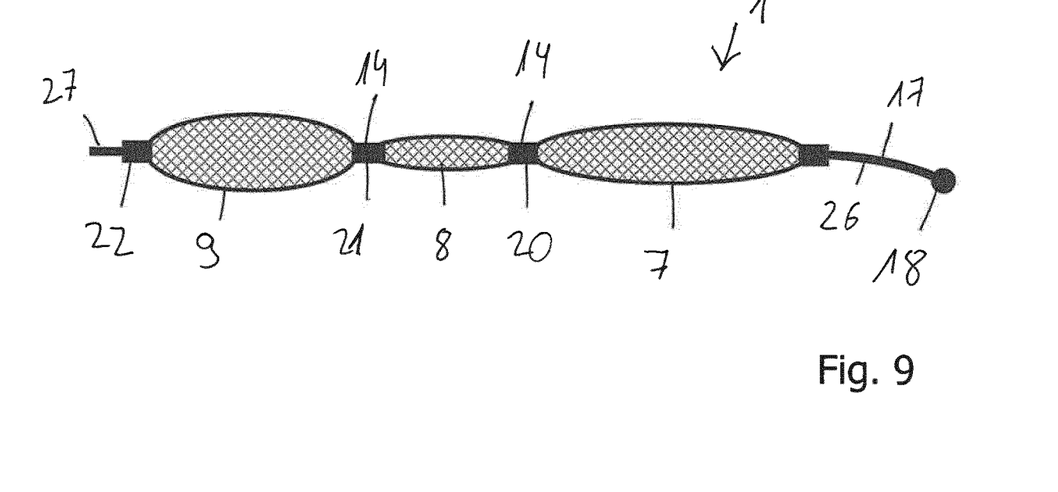
FIG. 9 shows a preferred embodiment of a braided device according to the invention in a schematic side view.

The bodies 2 are coupled to one another in a longitudinal direction 4 such that one of the bodies 2 is arranged distally 5 in the longitudinal direction, the other body 2 proximally 6 in the longitudinal direction 4 and the third body approximately midway between the two.

According to this preferred embodiment, the device 1 comprises in the longitudinal direction 4 from distal 5 to proximal 6 a first body 7 which is spindle-shaped and is intended for implantation in the isthmic section, a second body 8 which is spindle-shaped and is provided for implantation in the intramural section and a proximal body 9, which is also formed spindle-shaped and is intended for implantation in the uterine cavity.

The bodies 7, 8 and 9 have a predetermined radial expansion force in the expanded state. This expansion force is large enough or dimensioned such that the bodies can slightly expand a fallopian tube section which they contact, in order to bring about full circumferential contact of the bodies with the fallopian tube wall. This contact acts as a mechanical stimulus for body ingrowth into the fallopian tube wall. In addition, the radial expansion force must be dimensioned such that a contact portion 12 (FIG. 8) of an outer wall of the body 13 contacts the fallopian tube such that no chronic irritation, which is felt to be painful, or even penetration of the fallopian tube wall occurs. That means, the expansion force must be adjusted such that the contact portion 12 of the outer wall 13 of the bodies contact atraumatically with the corresponding portion of the Fallopian tube wall.

The bodies 7, 8 and 9 are braided from a plurality of wires so as to form a braided tubular endless structure. This structure is cut to length corresponding to a total length of the device 1 of approximately 35 mm to 45 mm at the proximal and distal ends 5, 6.

The bodies 7, 8 and 9 have a diameter of approximately 1 to 3 mm in the expanded state in the regions of their greatest extent transverse to the longitudinal direction of the device. In particular, the first distal body 7 and the third proximal body 9 have a larger diameter than the middle body 8, wherein preferably the proximal body 9 has a larger diameter than the distal body 7.

Figure 10:
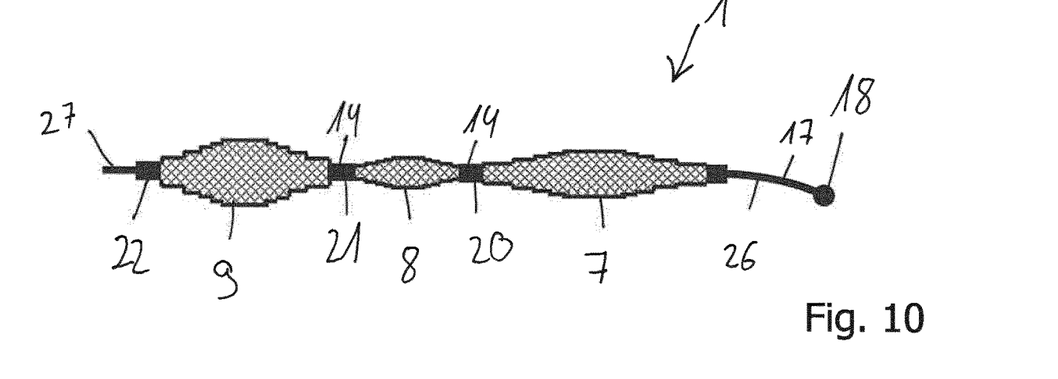
FIG. 10 shows a preferred embodiment of a laser-cut device according to the invention in a schematic side view.

FIG. 10 shows such a device whose grid structure has been produced by means of laser cutting. The spindle-shaped bodies also have a spindle shape in the laser-cut state. However, these include grid-related steps. These steps have a mechanical fixation effect in the fallopian tube, so that in laser-cut production, the use of funnel-shaped bodies is not absolutely necessary to achieve a fixation effect.

According to the preferred embodiment described above, the device according to the invention comprises three bodies, all three bodies being spindle-shaped (FIGS. 8, 9 and 10).

Figure 11:
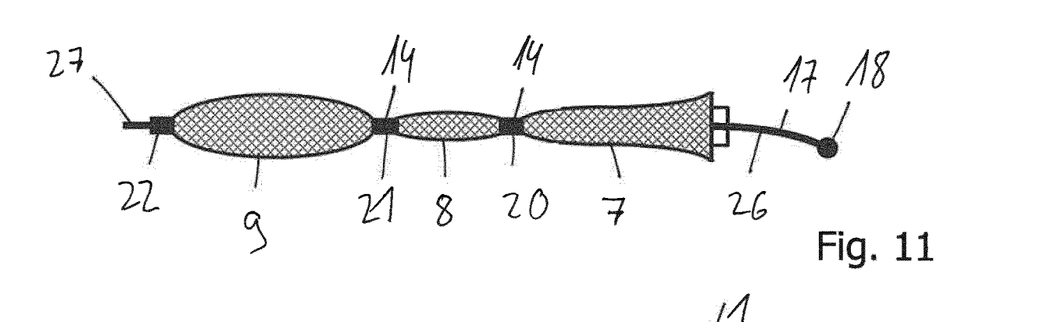
FIG. 11 shows a further preferred embodiment of a device according to the invention in a schematic side view.

According to an alternative preferred exemplary embodiment, wherein the arrangement of the bodies in the fallopian tube corresponds to the exemplary embodiment explained with reference to FIGS. 8 and 9, the third proximal and middle second bodies 8, 9 are spindle-shaped and the first distal body 7 is funnel-shaped (FIG. 11). Preferably, the proximal, first body 9 has a larger diameter than the distal body 7, and the distal first body 7 has a larger diameter than the middle second body 8.

Figure 12:
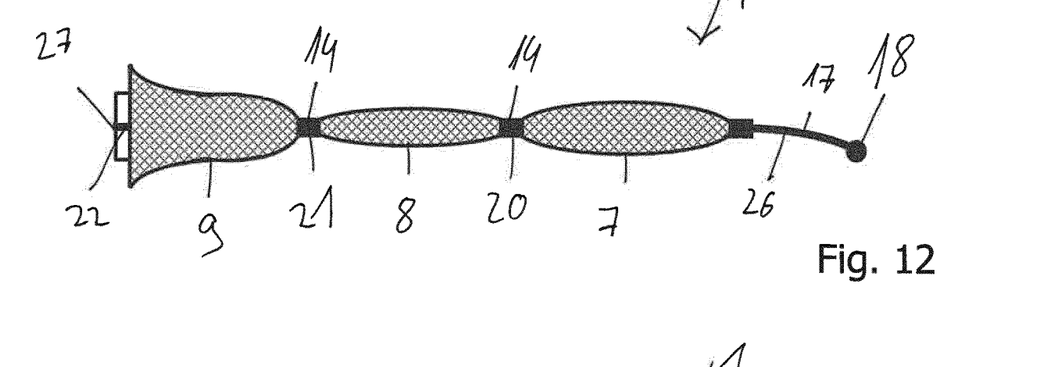
FIG. 12 shows a further preferred embodiment of a device according to the invention in a schematic side view.

Alternatively, the middle second and distal bodies 8, 7 may be spindle-shaped and the proximal third body 9 may be funnel-shaped (FIG. 12).

Figure 13:
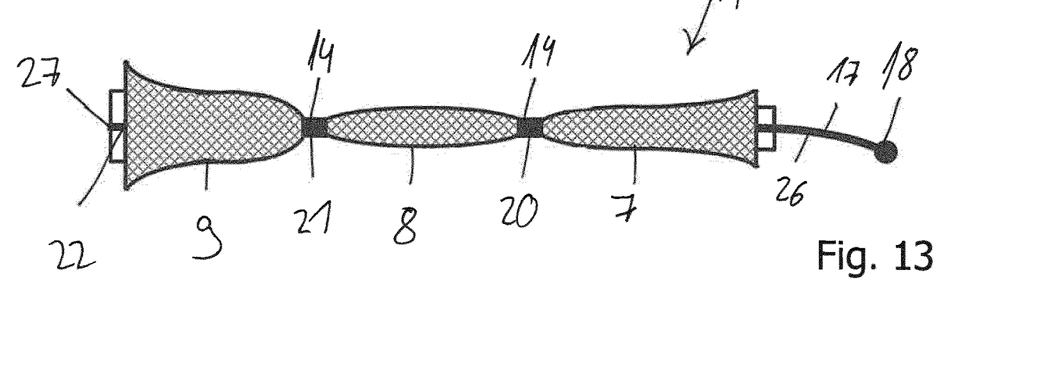
FIG. 13 shows a further preferred embodiment of a device according to the invention in a schematic side view.

Furthermore, it can also be provided that the third proximal and first distal bodies 9, 7 are funnel-shaped and the middle second body 8 is spindle-shaped. The proximal body may then be conically widening from distal to proximal or from proximal to distal. The distal body may then be conically widening from distal to proximal or from proximal to distal. However, it is preferred that according to such a design of the device, the proximal body from distally to the proximal and the distal body from proximal to distal are conically widening (FIG. 13). According to such a design of the device, the distal first and the proximal third funnel-shaped bodies are referred to as "locking funnels".

In the following, alternatives and details of the device according to the invention will be described.

Figure 7:
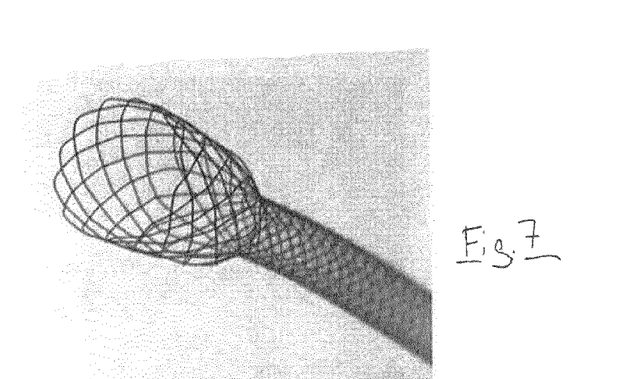
FIG. 7 shows a detailed view of an end of a funnel-shaped body of the device according to the invention.

FIG. 7 is a detail view of one end of a funnel-shaped body of the device according to the invention. Here it is provided that the proximal ends are formed into loops and therefore less traumatic.

The bodies according to the first and second embodiments are formed from a tubular endless structure, wherein the coupling sections are made by radial compression. The constrictions can be done by welding spots, gluing or just the sleeves described above.

It is then provided that only one probe tip is provided with an atraumatic ball at a distal end of the distal body.

A section between two bodies and/or a section of the connecting wire, which is arranged between two bodies and via which the bodies are coupled to one another, is referred to as a coupling section, wherein the coupling section is designed so flexibly that the bodies can be adapted to an anatomical course of a fallopian tube.

According to an alternative embodiment, the bodies may be braided from a single wire.

According to a further alternative, the bodies may be manufactured from a tubular body by means of laser cutting. In laser cutting, the radial expansion force can be adjusted by the following parameters: by the cutting pattern of the laser cut grid and by diameter, thickness and material of the tube semi-finished product and its shaping during tempering, wherein preferably a shape memory alloy such as Nitinol is applied.

Alternatively, the connecting wire 16 can also be made of a plurality of wires and thus strand-shaped or of a plurality of wires twisted together and thus shaped like a spiral coil. According to another embodiment, the connecting wire 16 may comprise an outer spiral coil wire comprising a central wire. This central wire forms a core to absorb the tensile forces acting on the connecting wire.

In providing a connecting wire, the bodies must be sufficiently spaced apart from each other, or, respectively, their distal and proximal sleeves must be sufficiently spaced apart from each other, to make the shortening on expansion such that they do not contact each other.

In all the embodiments described above, a proximal ejection wire section 27 may be provided, however, which does not take over a connection function between the bodies, but serves for better ejectability of the compressed implant arranged in a catheter.

Basically, the device or bodies must be designed such that after the device has been placed in the fallopian tube at the site of implantation and the catheter used for insertion is retracted, the bodies have sufficient freedom of movement in the longitudinal direction to take their fully expanded state.

As an alternative to self-expansion, the multiple bodies can be expanded sequentially or simultaneously by means of one or more balloon catheters.

FIG. 10 shows a perspective view of a cutting pattern of a connecting region of two bodies of the device according to the invention, produced by means of laser cutting, in a side view.

In case of producing the bodies by laser cutting in the diameter-changing intersections steps can be formed by the grid structure of the bodies due to radial deployment, e.g. at the proximal and distal end of a body and/or in the area between. Such steps are advantageous in that they exert an anchorage and fixation in contact with the fallopian tube wall against dislocation in the fallopian tube.

LIST OF REFERENCES 1 uterotubal implant device
2 body
3 grid structure
4 longitudinal direction
5 distally
6 proximally
7 first body
8 second body
9 third body
10 fourth body
11 fifth body
12 contact portion
13 outer wall
14 coupling section
15 sleeve
16 connecting wire
17 probe tip
18 atraumatic sphere
19 distal sleeve
20 sleeve
21 sleeve
22 sleeve
23 sleeve
24 sleeve
25 connecting wire section
26 distal wire section
27 proximal ejection wire section

The invention claimed is:

1. A uterotubal implant device comprising at least three compressible self-expandable bodies, the bodies being formed of a grid structure and coupled together in a longitudinal direction, wherein the at least three bodies comprise:
   a distal body at a distal end of the uterotubal implant device, wherein the distal body is a funnel-shaped body, which is formed to flare conically in a longitudinal direction with respect to the uterotubal implant device from a proximal end of the uterotubal implant device to the distal end of the uterotubal implant device;
   a proximal body at the proximal end of the uterotubal implant device, wherein the proximal body is a funnel-shaped body, which is formed to flare conically in a longitudinal direction with respect to the uterotubal implant device from the distal end of the uterotubal implant device to the proximal end of the uterotubal implant device; and
   a central body disposed between the proximal body and the distal body, wherein the central body is spindle-shaped body which is formed as a body which in a longitudinal direction with respect to the uterotubal implant device is conically flared at its proximal end and tapered at its distal end such that the central body forms a spindle shape.

2. The uterotubal implant device according to claim 1, wherein the at least three bodies in the expanded state have different diameters, wherein the central body has a smaller diameter in the expanded state than the proximal body and the distal body.

3. The uterotubal implant device according to claim 1, wherein a connecting wire or connecting wire sections are provided, which extend through the bodies in the longitudinal direction, wherein the bodies are connected at least at their proximal and/or distal ends with the connecting wire or the connecting wire sections, such that the coupling of the bodies is effected by means of the connecting wire, wherein the connecting wire or the connecting wire sections is formed of one or more wires of metal or plastic in a strand or coil shape of metal or plastic.

4. The uterotubal implant device according to claim 3, wherein a proximal end of the spindle-shaped central body is coupled by means of a sleeve to the connecting wire such that the proximal end of the body is longitudinally slidably connected to the connecting wire, and a distal end of the central body is fixedly connected to the connecting wire by means of a sleeve.

5. The uterotubal implant device according to claim 1, wherein at a distal end of the distal body, a distal wire portion, or at a distal end of a connecting wire or a connecting wire section, a probe tip is provided.

6. The uterotubal implant device according to claim 1, wherein a portion of the bodies and/or a section of a connecting wire arranged between two bodies, over which the bodies are coupled together, referred to as a coupling section, wherein the coupling section is flexible in such a way, that the bodies can be adapted to an anatomical course of a fallopian tube.

7. The uterotubal implant device according to claim 1, wherein the distal body is for implantation in the isthmic portion, a central body, for implantation in the intramural portion and a proximal body is for implantation in the uterine cavity.

8. The uterotubal implant device according to claim 1, wherein the length of the device from the distal end of the distal body to the proximal end of the proximal body accounts for 35 mm to 45 mm, and the diameter in the expanded state being about 1 mm to 4 mm.

9. The uterotubal implant device according to claim 1, wherein the distal body is arrangeable in the uterine cavity or uterotubal junction and has a diameter of about 3 mm to 4 mm, the central body is provided for implantation in the intramural portion and has a diameter of about 2 mm, and the proximal body is provided for implantation in the isthmic portion and has a diameter of about 3 to 4 mm.

10. The uterotubal implant device according to claim 1, wherein the proximal and distal bodies in the expanded state have a larger diameter and a greater radial expansion force than at least one intermediate body arranged therebetween.

11. The uterotubal implant device according to claim 1, wherein the bodies are braided from one or more wires or made of a tubular body by means of laser cutting, wherein openings of the bodies have an opening width from 300 μm up to 600 μm.

12. The uterotubal implant device according to claim 1, wherein the bodies in the expanded state have a predetermined radial expansion force large enough to expand to form a contact portion of an outer wall of the bodies to a fallopian tube wall, the contact portion generating a mechanical stimulus sufficient for ingrowth by the contact portion into the fallopian tube wall, and wherein the predetermined radial expansion force is suitable for atraumatic contact between a grid structure corresponding to the contact portion and the fallopian tube wall.

13. The uterotubal implant device according to claim 1, wherein outer surfaces of one or more bodies are completely or at least partially coated with a coating that may comprise one or more components, consisting of a polymer, wherein, the coating includes a hydrogel component and/or is doped with a bioactive agent and/or this drug is a spermicide and/or an anti-progesterone, which reduces bleeding and promotes implant ingrowth.

14. The uterotubal implant device according to claim 1, wherein the spindle-shaped central body is filled with a closure-promoting material and/or wherein the fibers are impregnated with hydrogel and/or that fibers are woven or braided in the grid structure to increase a spermicidal effect.

15. The uterotubal implant device according to claim 1, wherein the central body has its largest diameter in its center with respect to the longitudinal direction and is conically flared at its proximal end and conically tapered at its distal end such that it has an approximately elliptical cross-section.

16. The uterotubal implant device according to claim 1, further comprising another central body, wherein both central bodies have their largest diameter in their centers with respect to the longitudinal direction and are conically flared at their proximal ends and conically tapered at their distal ends such that they have an approximately elliptical cross-section.

17. A uterotubal implant device comprising at least three compressible self-expandable bodies, the bodies being formed of a grid structure and coupled together in a longitudinal direction, wherein the at least three bodies comprise:

a distal body at a longitudinally distal end of the uterotubal implant device, wherein the distal body is funnel-shaped and formed to flare conically toward the longitudinally distal end of the uterotubal implant device;

a proximal body at a longitudinally proximal end of the uterotubal implant device, wherein the proximal body is funnel-shaped and formed to flare conically toward the longitudinally proximal end of the uterotubal implant device; and a spindle-shaped central body which is formed as a body which in a longitudinal direction with respect to the uterotubal implant device is conically flared at its proximal end and tapered at its distal end such that the central body forms a spindle shape and disposed between the proximal body and the distal body.

* * * * *